(12) United States Patent (10) Patent No.: US 11,392,793 B2
Masuda et al. (45) Date of Patent: Jul. 19, 2022

(54) BLOOD VESSEL EXTRACTION DEVICE AND BLOOD VESSEL EXTRACTION METHOD

(71) Applicant: Nemoto Kyorindo Co., Ltd., Tokyo (JP)

(72) Inventors: Kazumasa Masuda, Tokyo (JP); Shigeru Nemoto, Tokyo (JP); Wataru Uda, Tokyo (JP); Arashi Haishima, Tokyo (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 151 days.

(21) Appl. No.: 16/651,885

(22) PCT Filed: Oct. 1, 2018

(86) PCT No.: PCT/JP2018/036733
§ 371 (c)(1),
(2) Date: Apr. 27, 2020

(87) PCT Pub. No.: WO2019/069867
PCT Pub. Date: Apr. 11, 2019

(65) Prior Publication Data
US 2020/0327370 A1 Oct. 15, 2020

(30) Foreign Application Priority Data
Oct. 3, 2017 (JP) .............................. JP2017-193805

(51) Int. Cl.
*G06N 3/08* (2006.01)
*G06V 10/22* (2022.01)
(Continued)

(52) U.S. Cl.
CPC ............. *G06K 9/6256* (2013.01); *G06N 3/08* (2013.01); *G06V 10/22* (2022.01); *G06V 20/64* (2022.01); *G16H 30/20* (2018.01); *G06V 2201/03* (2022.01)

(58) Field of Classification Search
None
See application file for complete search history.

(56) References Cited

U.S. PATENT DOCUMENTS

2004/0170308 A1 9/2004 Belykh et al.
2015/0173707 A1 6/2015 Ohuchi et al.
(Continued)

FOREIGN PATENT DOCUMENTS

EP 2826415 A1 1/2015
EP 3171297 A1 5/2017
(Continued)

OTHER PUBLICATIONS

Kanai et al., "By convolutional neural network using 3D filter 3D object recognition". Hosei University Graduate School of Informational Science., 2016.
(Continued)

*Primary Examiner* — Idowu O Osifade
(74) *Attorney, Agent, or Firm* — Knobbe, Martens, Olson & Bear, LLP

(57) ABSTRACT

A blood vessel extraction apparatus including a convolutional neural network including a convolution unit which has a first path to which data for a first target region including some target voxels in medical volume data is input at a first resolution, and a second path to which data for a second target region including some target voxels in the medical volume data is input at a second resolution; and an output unit having a neural net structure which outputs numerical values related to visualization of the target voxels with an
(Continued)

output result of the first path and the second path as input data.

8 Claims, 7 Drawing Sheets

(51) Int. Cl.
  *G06V 20/64* (2022.01)
  *G06K 9/62* (2022.01)
  *G16H 30/20* (2018.01)

(56) References Cited

U.S. PATENT DOCUMENTS

| | | | |
|---|---|---|---|
| 2017/0277977 | A1 | 9/2017 | Kitamura |
| 2018/0165808 | A1* | 6/2018 | Bagci ............... A61B 6/032 |
| 2018/0240235 | A1* | 8/2018 | Mazo ............... G06T 7/0012 |
| 2021/0312622 | A1* | 10/2021 | Buckler ............ G06K 9/6267 |
| 2021/0334963 | A1* | 10/2021 | Isgum .................. G06T 7/10 |

FOREIGN PATENT DOCUMENTS

| | | |
|---|---|---|
| JP | H08-24227 | 1/1996 |
| JP | A 2013191007 | 9/2013 |
| JP | A 2015119768 | 7/2015 |
| JP | A 2017174039 | 9/2017 |

OTHER PUBLICATIONS

Kitrungrotsakul et al. Automatic Vessel Segmentation using A Combined Deep Network. JAMIT Annual Meeting, pp. 379-382, Jul. 27, 2017.

Osareh et al. "An Automated Tracking Approach for Extraction of Retinal Vasculature in Fundus Images". Journal of Ophthalmic and Vision Research, vol. 5, No. 1, pp. 20-26, 2010.

International Search Report for International Application No. PCT/JP2018/036733 dated Dec. 12, 2018.

International Preliminary Report on Patentability for for International Application No. PCT/JP2018/036733 dated Dec. 12, 2018.

Kloenne et al. "Domain-Specific Cues Improve robustness of deep learning-based segmentation of CT volumes", Nature, vol. 10:10712, 2020.

Kamnitsas et al. "Multi-Scale 3D Convolutional Neural Networks for Lesion Segmentation in Brain MRI". Biomedical Image Analysis Group, Imperial College London, UK, MICCAI Ischemic Stroke Lesion Segmentation Challenge, 2015.

Lee et al. "Practical Window Setting Optimization for Medical Image Deep Learning". Machine Learning for Health, Workshop at NeurIPS, pp. 1-7, Dec. 3, 2018.

Extended European Search Report in European Patent Application No. 18865027.9, dated May 10, 2021.

* cited by examiner (a)　　　　　　　　　(b)

BLOOD VESSEL EXTRACTION DEVICE AND BLOOD VESSEL EXTRACTION METHOD

This application is the U.S. National Phase under 35 U.S.C. § 371 of International Application No. PCT/JP2018/036733, filed Oct. 1, 2018, designating the U.S., and published in Japanese as WO 2019/069867 on Apr. 11, 2019, which claims priority to Japanese Patent Application No. 2017-193805, filed Oct. 3, 2017, the entire contents of which are incorporated herein by reference.

TECHNICAL FIELD

The present invention relates to a blood vessel extraction apparatus and a blood vessel extraction method, particularly to a blood vessel extraction apparatus and a blood vessel extraction method that enable to save work of an operator, and to extract a blood vessel with high accuracy from medical volume data.

BACKGROUND ART

As medical imaging diagnosis apparatuses, X-ray CT (Computed Tomography) apparatuses, MRI (Magnetic Resonance Imaging) apparatuses, PET (Positron Emission Tomography) apparatuses, ultrasonic diagnostic apparatuses, and angiographic imaging apparatuses have heretofore been known.

Moreover, three-dimensional imaging of an interior of a body of a subject has also been carried out by using imaging data acquired by such imaging apparatus. For instance, Patent Document 1 discloses extracting a region of a coronary artery by segmentation processing on the basis of CT volume data achieved by photographing a vicinity of a heart by an X-ray CT apparatus.

PRIOR ART DOCUMENT

Patent Document

Patent Document 1: Japanese Patent Application Laid-open Publication No. 2015-119768

SUMMARY OF THE INVENTION

Problems to be Solved by the Invention

Incidentally, until now, in a case of making an attempt to extract a blood vessel such as coronary artery for instance, from a medical volume data, a job of determining an outline of the blood vessel while viewing a plurality of cross-sectional images of the blood vessel by an operator becomes necessary. Or, generally, even in a case of carrying out the extraction automatically by software, a job such as carrying out setting of a threshold value necessary for the automatic extraction becomes necessary.

Whereas, the inventors of the present invention found that it is possible to extract a target blood vessel effectively by applying a convolutional neural network technology, thereby saving such jobs of the operator.

Therefore, an object of the present invention is to provide a blood vessel extraction apparatus and a blood vessel extraction method that enable to save jobs of the operator and to extract a blood vessel with high accuracy from medical volume data.

Means for Solving the Problems

A blood vessel extraction apparatus according to an aspect of the present invention for solving the problem is as follows:

a blood vessel extraction apparatus which extracts from medical volume data, a blood vessel in the medical volume data by using a convolutional neural network, wherein the convolutional neural network is characterized by including a convolutional unit having a1: a first path including a plurality of convolutional layers, to which, data for a first target region including some target voxels in the medical volume data, is input at a first resolution, and a2: a second path including a plurality of convolutional layers, to which, data for a second target region including some target voxels in the medical volume data, is input at a second resolution, and b: an output unit having a neural net structure, which outputs numerical values related to visualization of the target voxels with an output result of the first path and the second path as input data.

(Description of Terminology)

'Convolutional neural network' refers to a network which includes at least one convolutional layer (CNN: Convolutional Neural Network), and which carries out extraction of features by executing convolution processing on image data input (also includes three-dimensional image data), by that convolutional layer. As a filter to be used for the convolution processing, a three-dimensional filter is prepared for three-dimensional input data, and a numerical value (weight) referred to as a so-called filter parameter has been set for each component (element) of the filter.

'Data related to visualization' refers to a numerical value (voxel values) imparted to each voxel for instance, and is a value that enables to determine as to whether or not that voxel is to be displayed, or in a case of displaying, as to with what degree of brightness the voxel is to be displayed, corresponding to that numerical value. For example, they are values in the range of '0' to '1'.

Effects of the Invention

According to the present invention, it is possible to provide a blood vessel extraction apparatus and a blood vessel extraction method that enable to save work of an operator, and to extract a blood vessel with high accuracy from medical volume data.

EMBODIMENTS FOR CARRYING OUT THE INVENTION

1. Basic Configuration

Figure 1:
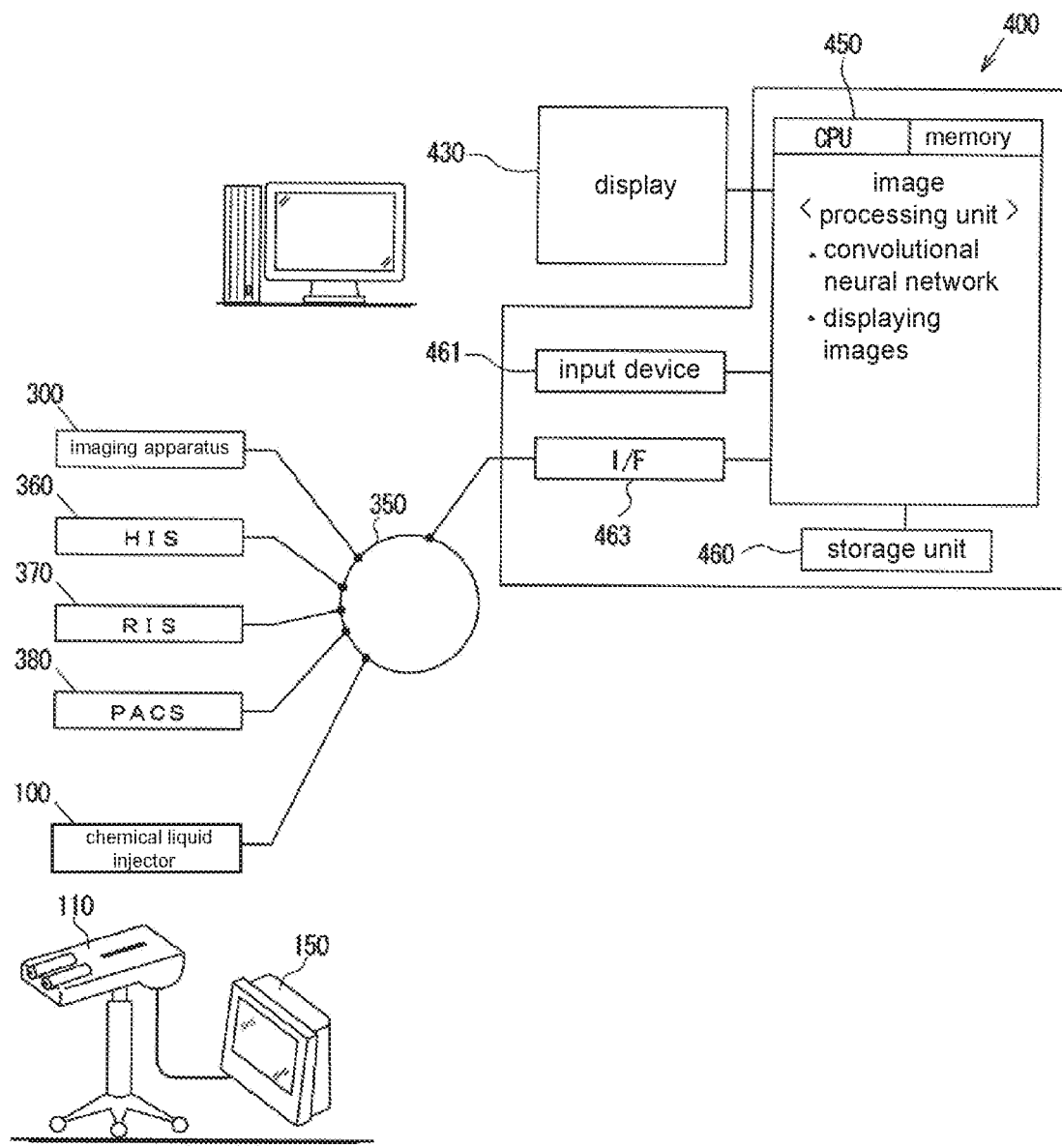
FIG. 1 is a diagram showing schematically a system including a blood vessel extraction apparatus of one aspect of the present invention.

FIG. 1 is a diagram showing schematically a configuration of an overall system including a blood vessel extraction apparatus according to one aspect of the present invention. As the overall system, in one example, may include an imaging apparatus 300, an HIS 360 which is a medical record management apparatus, an RIS 370 which is an imaging management apparatus, a PACS 380 which is a data storage unit, a chemical-liquid injector 100 which injects a contrast medium into a patient, a blood vessel extraction apparatus 400, a network 350 which connects these apparatuses, and the like. Note that, for a configuration other than the blood vessel extraction apparatus 400, a conventionally known configuration may be used.

The HIS (Hospital Information System) 360 is a computer having a dedicated computer program installed therein, and has a medical record management system. An electronic medical record managed by the medical record management system may be an electronic medical record including data such as a medical record ID which is specific identification information, a patient ID for each patient, personal data such as a name etc. of a patient, medical record related to an illness of the patient, and the like. Moreover, weight, sex, age etc. of a patient may be recorded as personal condition data associated with general treatment.

The RIS (Radiology Information System) 370 manages imaging order data for imaging fluoroscopic image data of a patient, with specific identification information. The imaging order data may be data that is to be created on the basis of an electronic medical record acquired from the HIS. The imaging order data may include data such as an imaging job ID which is specific identification information, type of job such as CT imaging, MR imaging, and the like, a patient ID and medical record data of the aforementioned electronic medical record, identification information of a CT scanner, date and time of start and end of imaging, body part or imaging part, appropriate classification including chemical liquid type such as a contrast medium suitable for the imaging job, an appropriate ID including the chemical liquid ID suitable for the imaging job, and the like.

The PACS (Picture Archiving and Communication Systems) 380 receives the fluoroscopic image data to which the imaging order data is imparted from the imaging apparatus, and stores it in a storage unit.

The imaging apparatus 300 is an X-ray CT apparatus for example, and may include an imaging apparatus which images a fluoroscopic image of the patient, a bed for the patient, and a control unit which controls those operations. The imaging apparatus may have an X-ray irradiating unit disposed inside a gantry, having an X-ray tube, a collimator and the like, which irradiates X-ray toward the patient, and a detecting unit having an X-ray detector which detects X-ray transmitted through the patient. The X-ray irradiating unit and the detecting unit are configured to carry out scanning while revolving around a body axis of the patient with a positional relationship thereof maintained as it has been.

Figure 2:
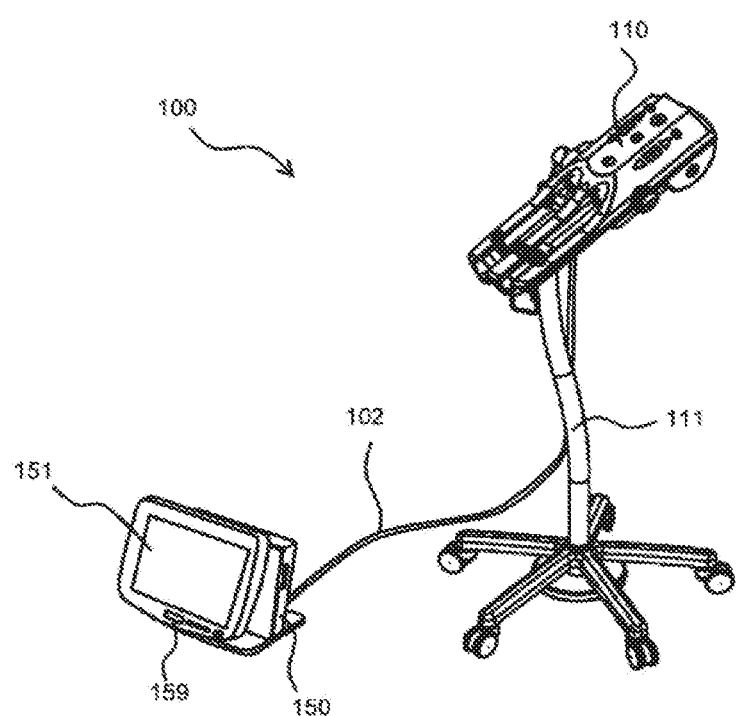
FIG. 2 is a perspective view showing an example of a chemical-liquid injector.

The chemical-liquid injector 100 will be explained below by referring to FIG. 2 as well. The chemical-liquid injector 100 includes for example, an injection head 110 held by a movable stand 111 and a console 150 connected to the injection head 110 by a cable 102. In this example, two syringes are removably mounted in parallel. The injection head 110 and the console 150 may have been connected by a wireless system.

Chemical liquids to be filled in the syringes include contrast media, physiological saline solutions, and the like. For example, one syringe may be filled with a contrast medium and the other syringe may be filled with a physiological saline solution. The syringe has a cylinder member having a hollow cylindrical shape, and a piston member which is slidably inserted into the cylinder member. The cylinder member may have a cylinder flange formed at a base-end portion thereof, and a conduit portion formed at a front-end portion thereof. By sliding down the piston member into the cylinder member, the chemical liquid in the syringe is pushed outside via the conduit portion. The syringe may be of a pre-filled type in which a chemical liquid has been filled in advance, or of a suction type which is used by sucking the chemical liquid into the empty syringe.

Illustration in detail of the injection head is omitted; however, it may be an injection head as follows. In other words, as an example, the injection head has a housing that can be extended to be long in a frontward-rearward direction, and two recesses in which the syringes are mounted respectively are formed in an upper-surface front-end side of the housing. The recesses are portions functioning as syringe holding portions. The syringe may be mounted directly in the recess, or may be mounted via a syringe adapter.

The injection head, moreover, has a piston-drive mechanism which has at least a function of pushing the piston member of the syringe. Two lines of piston-drive mechanism are provided, and each mechanism operates independently. The piston-drive mechanism may be a mechanism having a function of backing off the piston member for filling a chemical liquid. The two piston-drive mechanisms may be driven simultaneously or may be driven at different timings. An illustration in detail of the piston-drive mechanism is omitted; however, the piston-drive mechanism may include a drive motor, a motion conversion mechanism which converts a rotation output of the drive motor to a linear motion, and a syringe presser (ram member) which is connected to the motion conversion mechanism, and which makes the piston member move forward and/or backward.

As such piston-drive mechanism, it is possible to use a known mechanism that is normally used in a chemical-liquid injector. Note that, an actuator other than motor may be let to be a drive source. Instead of 'piston-drive mechanism', a drive mechanism which delivers toward the patient a chemical liquid from a predetermined chemical-liquid accommodating body (such as bottle, bag and the like) other than syringe may have been provided.

In a case in which an IC tag (identification tag) is put on the syringe, the injection head may have a reader/writer which reads information of the IC tag and/or writes information in the IC tag. The reader/writer may have been provided to the recess in which the syringe is mounted. The reader/writer may have only a function of reading the information of the IC tag.

The console 150 may be placed in a control room adjacent to an examination room, and used. The console 150 includes a display 151 which displays a predetermined image, an operation panel 159 provided to a front surface of the housing, a control circuit disposed inside the housing, and the like. The operation panel 159 is a portion on which, one or a plurality of physical buttons are disposed, and is to be operated by a user. The display 151 may be a touch-panel type display device or may be simply a display device. The console 150 may include a speaker etc. (not shown) for outputting sound and/or voice. Various data related to creating an injection protocol and execution of injection may be stored in a storage section (not shown) of the console. The data includes data of a graphical user interface, injection conditions (injection pattern) and the like.

(Blood Vessel Extraction Apparatus)

The blood vessel extraction apparatus 400 includes an input device 461, an image processing unit 450, an interface 463, a storage unit 460, and the like for example. Commonly-used devices such as a keyboard, a mouse and the like can be cited as the input device 461, According to the requirement, a microphone (MIC) and the like for inputting sound may be used. It is not restricted, but the blood vessel extraction apparatus 400 may include a work station, a laptop computer, a tablet terminal and the like. The blood vessel extraction apparatus 400 is not necessarily required to be physically separate equipment, and may be realized by one or a plurality of computers in the network for example. Moreover, the blood vessel extraction apparatus 400 may have been provided as a part of an imaging apparatus or may have been provided as a part of a chemical liquid. Specifically, a computer program according to an aspect of the present invention may be realized by installing in a console of the imaging apparatus, or by installing in one or a plurality of computers in the network, or by installing in a console etc. of the chemical liquid injector in order to provide the blood vessel extraction apparatus.

The interface 463 is for connecting to various external instruments etc., and although only one is illustrated in FIG. 1, as a matter of course, may have been provided in plurality. A method of connection (method of communication) may be wired or may be wireless. In the example in FIG. 1, the imaging apparatus 300 is connected to the interface 463 via the network, and accordingly, data of the imaging apparatus 300, the PACS 380, and the like is read by the blood vessel extraction apparatus 400 (or is identified by that apparatus).

The storage unit 460 may include a hard disc drive (HDD—Hard Disk Drive), a solid state drive (SSD: Solid State Drive), and/or a memory, and may have a computer program of an OS (Operating System) and a blood vessel extraction program according to an aspect of the present invention stored therein.

Moreover, other computer programs, data tables, image data and the like to be used in various processing may have been stored in the storage unit 460 according to the requirement. A computer program is executed by being loaded in a memory of a processor (CPU, GPU, and the like). A computer program may be downloaded partly or fully from external equipment when needed, via an arbitrary network. Computer programs may be stored in a computer-readable recording medium.

The blood vessel extraction apparatus 400 is configured to display predetermined information on a display 430. As the display 430, it is not restricted in particular, and an LCD (Liquid Crystal Display), an organic EL (Electro-Luminescence) display, and the like, can be used. In a case in which the blood vessel extraction apparatus 400 is configured as a single housing, the display 430 may be provided integrally to a part thereof. Or, may be separate from the main body (not shown), and used by connecting.

(Configuration of Image Processing Unit)

The image processing unit 450 is configured to carry out predetermined image processing and computing of machine learning by operating a processor and the like according to a command of a computer program. It is not restricted; however, since the image processing unit 450, in one embodiment, carries out convolutional processing in the neural network as it will be described later, it is preferable that the image processing unit 450 uses GPU (Graphics Processing Unit).

2. Configuration and Operation of Neural Network

[Configuration]

Figure 3:
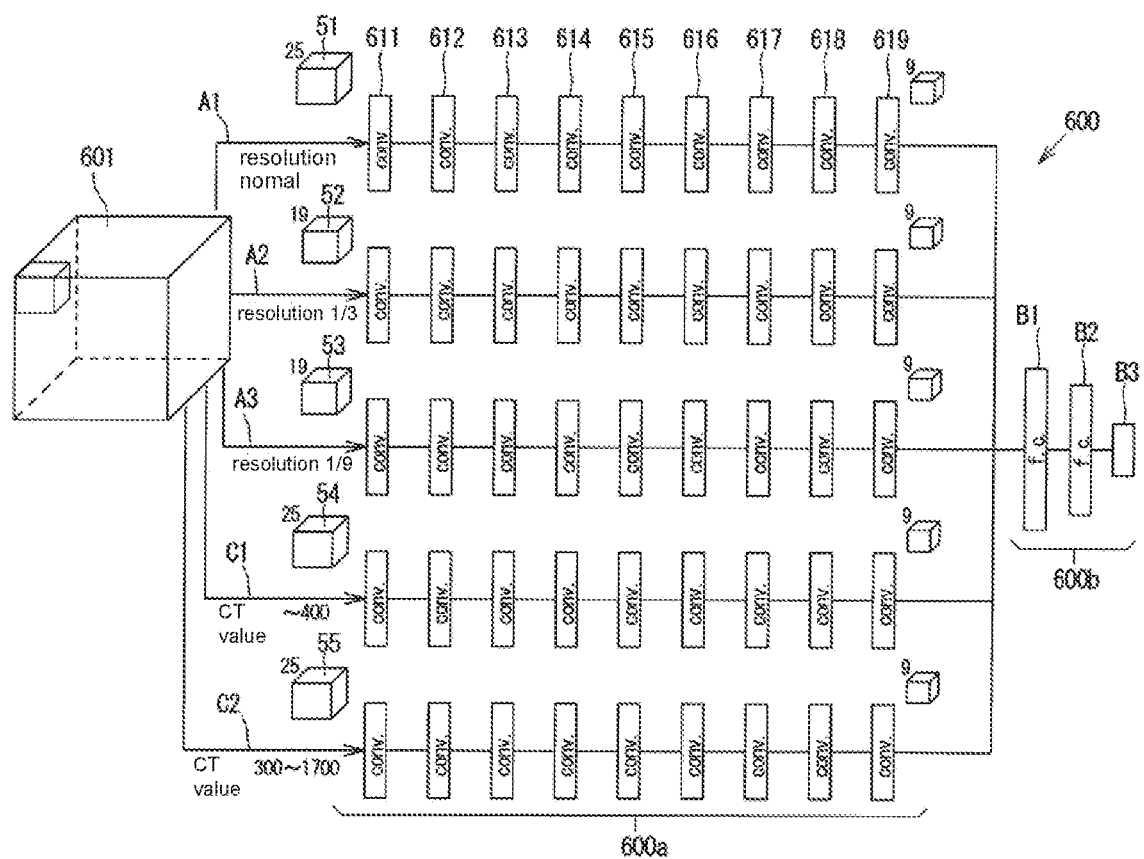
FIG. 3 is a diagram showing a configuration of a convolutional neural network.

An example of the neural network used in the present embodiment is shown in FIG. 3. As shown in FIG. 3, a convolutional neural network 600 includes a convolutional unit 600a in which, a plurality of paths carrying out a convolution processing is disposed in parallel and an output unit 600b in continuity with the convolution unit 600a. A function of each path in the convolution unit 600a is basically similar, but according to a type of data that is input, the paths are distinguished as paths A1 to A3 and additional paths C1 to C2 (also called simply as a path C1 and a path C2) in the following description.

(First Path A1)

A first path A1 includes a plurality of convolutional layers 611 to 619 that carry out the convolution processing. The convolutional layers 611 to 619 carry out convolution of three-dimensional data that has been input (details below), by using a three-dimensional filter which is not shown in the diagram.

The number of convolutional layers is not restricted in particular; however, in this example, there are nine layers. The number of layers may be increased or decreased according to the requirement. A filter of a filter size 3×3× for example, can be used as the three-dimensional filter. Filter parameters (weight) are set for each element (in this case, 3×3×3=27 elements) of the filter. As filter parameters, as an example, it is possible to use a data set adjusted to appropriate values according to machine learning in advance.

Note that, a moving distance (sliding) of filter at the time of convolution process is not restricted, and may be one voxel at a time or may be two voxels at a time for example.

In the present embodiment, data 51 input to the first path A1 is three-dimensional data of 25×25×25 (detailed contents will be described later). By letting it to be subjected to convolution sequentially in each convolutional layer, a size of one side decreases to '25'→'23'→'21'→'19'→'17'→'15'→'13'→'11', and finally, a size of 9×9×9 is obtained.

(Other Paths A2, A3, C1, C2)

Even regarding the other paths A2, A3, C1, and C3, basically, they are similar to the abovementioned path A1, and each of them has nine convolutional layers. However, the data that is input differs. While the details will be described later, for the paths A2 and A3, data in which a resolution differs from that of the first path A1 is input. In other words, in this embodiment, letting a multi-resolution to be the input data, a method of applying to a different path has been adopted. Whereas, for the additional paths C1 and C2, data in which, a range of CT values is let to differ and not a difference in resolution, is let to be the input data.

Note that, in FIG. 3, although a size of data input to the paths A2 and A3 is displayed as one side '19', it is not an essential part of the present invention, and an arrangement may be made to input data of 25×25×25 size. Moreover, as another note, in the paths A2, A3, the input data being 19×19×19, the size at a stage of eighth layer becomes 3×3×3. Therefore, an up-sampling processing (a processing for making a size of an object generated by the convolution processing) is executed so that a size of output data of each path become finally the same (in other words, so that the size becomes 9×9×9).

(Input Data)

Next, details of an input image will be described by referring to FIG. 4. Note that, in FIG. 4, for convenience of description, it is expressed as a two-dimensional image. Moreover, for simplifying the description, even for data 52 and 53 that is input to the paths A2 and A3, the size of one side is indicated as '25' and not '19'.

Figure 5:
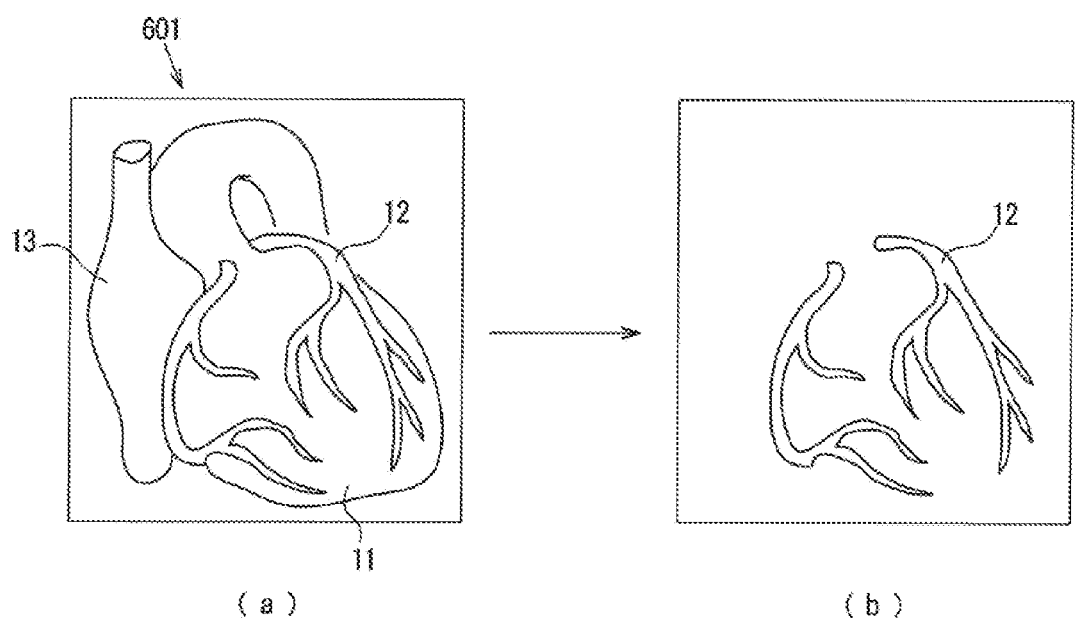
FIG. 5 is a diagram showing CT volume data, and blood vessels extracted automatically from the CT volume data.

Medical volume data 601 may be CT volume data of a vicinity of heart as shown in FIG. 5(*a*) for instance. In this example, the volume data 601 includes a heart 11 and a coronary artery 12, and further includes a blood vessel 13 such as a large artery and a large vein, a bone (not shown), and the like. It is not restricted, but a size of the medical volume data as an example, is 512×512×512. Note that, as the medical volume data, it may be data which is created by a conventional known method by using imaging data acquired by imaging a subject in advance by an X-ray CT apparatus and the like. For instance, CT volume data stored in a predetermined server in the network may be read out and used.

Figure 4:
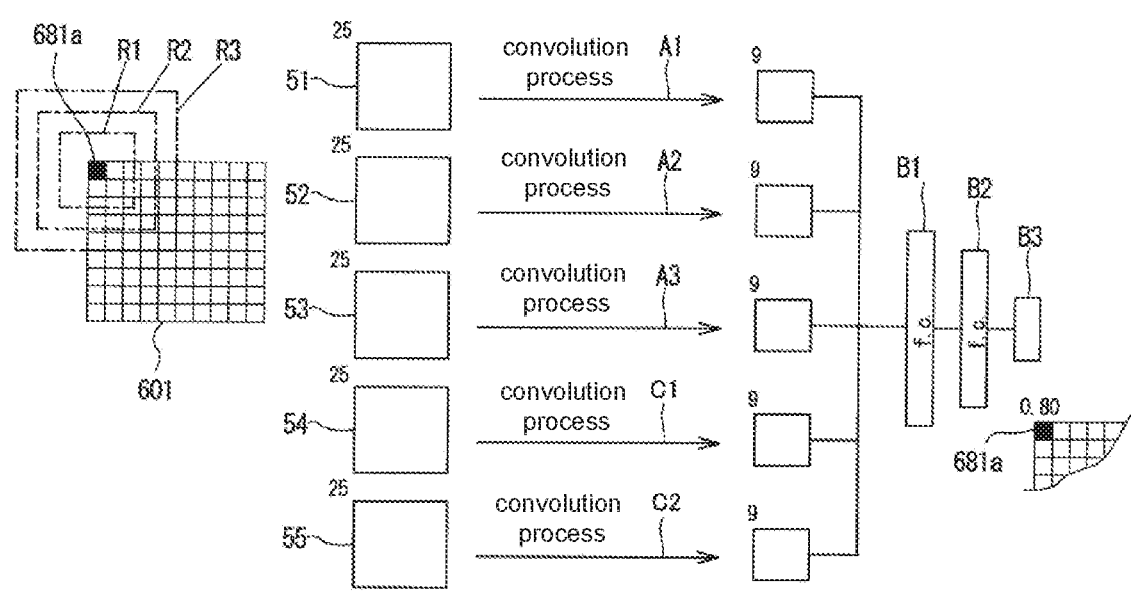
FIG. 4 is a diagram for explaining a function of the convolutional neural network in FIG. 3.

The data 51 which is input to the first path A1, as shown in FIG. 4, is data of a first target region R1 including one voxel 681*a* in the medical volume data 601 and a region in a predetermined range around the voxel 681*a*. The first target region R1, for instance, may be data in a range of 25×25×25 with the voxel 681*a* as a center, The data 52 which is input to the second path A2 is almost common to the aforementioned, as data of a region with the voxel 681*a* as a center. However, for letting to be an input of the multi-resolution, the following processing is carried out. In other words, a target region R2 larger than the first target region R1 is subjected to sampling, and is let to be the data 52 of a desired size by lowering the resolution for that. Specifically, an arrangement may be made to achieve the data 52 of 25×25×25 by letting the target region R2 to be of $(25 \times 3)^3$, and lowering the resolution to ⅓. However, the size of one side may be '19' and not '25' as aforementioned, and in this case, it becomes the second target region R2 of $(19 \times 3)^3$.

Even regarding the data 53 which is input to the third path A3, the concept is similar to the case of the second path A2. However, regarding the data 53, it is let to be a target region R3 of $(25 \times 9)^3$ and the resolution is lowered to ⅑. Note that, a size of the R2 and the R3 illustrated in FIG. 4 is a schematic size, and not an actual size indicated accurately.

Data 54 and 55 input to the paths C1 and C2 have a size similar to that of the data 51 of the first path A1, but differs at a point that the CT value is clipped (restricted) within a predetermined range. In other words, only data within that range of the CT value is input. This will be described below while referring also to FIG. 6.

Figure 6:
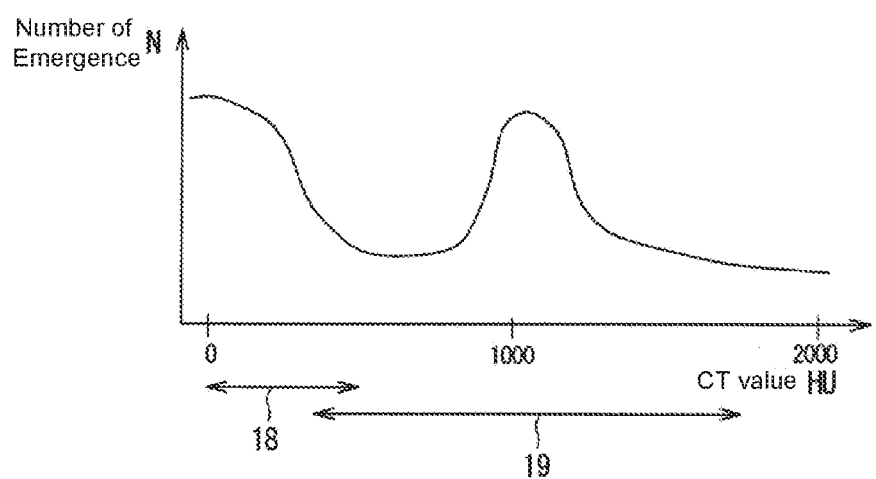
FIG. 6 is a schematic histogram of voxel values in the CT volume data.

FIG. 6 is a diagram in which a histogram of the CT values of voxels included in the medical volume data 601 is shown schematically. A horizontal axis is the CT value (HU), and a vertical axis is the number of emergence (N). In such manner, generally, a histogram of the medical volume data becomes data for which a peak exists at a location such as a soft tissue and moisture at which the CT value is relatively low, and a location including a bone/calcified tissue at which the CT value is relatively high. Specifically, the CT values for water and air are 0 HU and −1000 HU respectively, whereas for a soft tissue and the like (soft tissue, blood, brain, organ substance) is about 20 to 100 HU, for bone/calcified tissue is about 1000 HU, and for fat is about −100 HU.

In FIG. 6, a range 18 is a range of a lower side of the CT value with an upper limit of about 500 HU, and a range 19 is a range of a higher side of the CT value with a lower limit of about 300 HU. The specific value is not restricted in particular, and is to be set appropriately according to diagnosis type and a body part of interest of a patient etc. For the range 18, the lower limit may be 1000 HU, −200 HU, −100 HU, or 0 HU. In a case of coronary artery extraction, specific examples of the range 18 include a range 0 to 500 HU or 0 to 400 HU. Specific examples of the range 19 include a range 300 to 2000 HU or a range 300 to 1700 HU.

An arrangement is made to input data reduced to the range of the lower side of the CT value to the path C1 upon dividing the medical volume data 601 into the range of the CT value in such manner, and to input data reduced to the range of the higher side of the CT value to the path C2.

Note that, the input data 51 to 55 have been explained in the abovementioned description, and with regard to carrying out the data processing in the convolutional neural network, preprocessing such as batch normalization and whitening, converting the CT values of voxels into a certain numerical range (numerical value in this case is also called as 'voxel value') according to the requirement may be carried out.

Next, the output unit 600*b* of the convolutional neural network 600 will be described. The output unit 600*b* is a neural network structure including fully connected layers B1 and B2, and an output layer B3. Note that, even in this case, the number of fully connected layers is not restricted in particular, and may be one layer or three or more than three layers. An output results of the paths A1 to A5 are input to the fully connected layer B1, In other words, the numerical value of each element of three-dimensional data which is the output result of the paths A1 to A5 is connected to a node (not shown) of the fully connected layer B1.

Note that, the 'fully connected layer', basically, literally refers to a network of a feed forward type in which all the nodes are connected; however, in relation to the technical concept of the present application; all the nodes are not necessarily required to be connected strictly.

Figure 8:
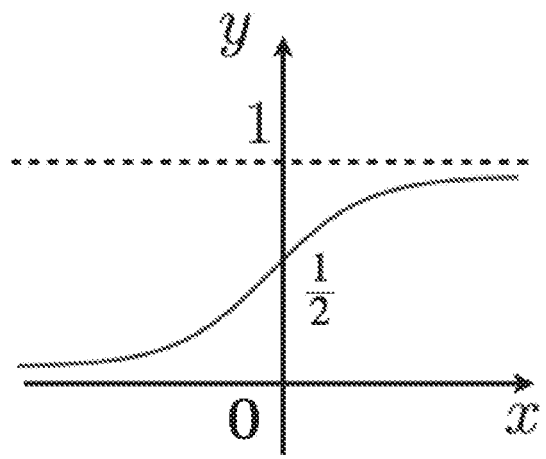
FIG. 8 is a graph showing an example of an activation function.

The output layer B3 is a layer which carries out the final output on the basis of data from the fully connected layer B2, and in this example, outputs numerical data of a range from '0' to '1'. This can be considered as a probability indicating whether or not the target voxel 681*a* is a coronary artery; and an arrangement may be made such that, when it is 1 (or near 1), it is let to be a coronary artery, and when it is 0 (or close to 0), it is not let to be a coronary artery. For achieving such output, it is possible to use various activation functions, and for example, a sigmoid function and the like can be used. As shown in FIG. 8, the sigmoid function is a function which carries out an output (y) in the range of '0' to '1' for x that has been input.

[Operation]

Next, an operation of a multi-layer neural network of the present embodiment will be described. Note that, as a prerequisite, weight parameters (not shown) of the network will be let to be parameters that have already been imparted by the machine learning in advance for instance.

To begin with, the image processing unit 450 (refer to FIG. 1), either identifies or reads the medical volume data 601 prepared in advance.

Figure 7:
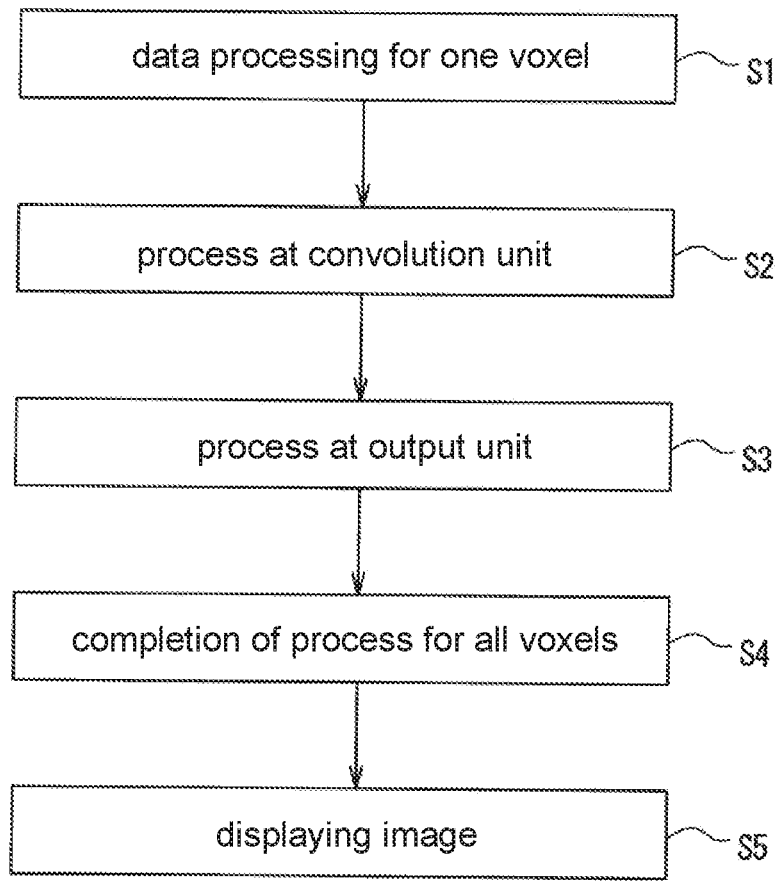
FIG. 7 is a flowchart of a processing in the convolutional neural network in FIG. 3.

Next, as shown in a flowchart in FIG. 7, a data processing intended for one voxel 681*a* (refer to FIG. 4) is carried out (step S1). By a function of the abovementioned multi-layer neural network 600, convolution processing of the three-dimensional input data 51 to 55 is carried out in a convolutional neural network unit 601*a* (step S2) and a feed-forward computation processing in the output unit 600*b* is carried out, and finally, in the output layer B3, numerical data indicating whether or not the voxel 681*a* is a coronary artery is calculated (step S3, also refer to FIG. 4).

A similar processing is to be executed repeatedly for all the voxels of the medical volume data 601 (step S4). Accordingly, all the voxels can be subjected to numerical conversion in the range of 0 to 1. By carrying out image display only for a predetermined voxel on the basis of the data achieved in such manner, it is possible to generate a three-dimensional image in which only the coronary artery 12 is extracted, as shown in FIG. 5(*b*) (step S5).

A specific method for image display is not restricted in particular, and for example, the voxel value is compared with a predetermined threshold value, and when the voxel value is more than the threshold value, the voxel is to be displayed, and when the voxel value is not more that the threshold value, the voxel is not to be displayed (or may be displayed in a state in which the brightness is lowered).

According to the blood vessel extraction method described above in which the convolutional neural network 600 is used, since only a blood vessel 12 which is intended, is extracted automatically as shown in FIG. 5(*b*) only by inputting the medical volume data 601 as in FIG. 5(*a*), it is possible to execute the blood vessel extraction extremely effectively.

Moreover, in the multi-layer neural network 601, by using a data set of the weight parameter which is within the appropriate numerical range, it is possible to obtain a blood vessel shape (FIG. 5(*b*)) in which an actual blood vessel shape (blood vessel shape in FIG. 5(*a*).) has been reproduced with high accuracy. The present embodiment, basically, is a method of displaying only the coronary artery by not displaying unnecessary voxels, on the basis of the medical volume data 601. Accordingly, for instance, unlike in a method in which a path of a center of a blood vessel is created and a certain fixed radius portion with respect to that path is regarded as a blood vessel and displayed, a possibility of displaying a voxel which is not a coronary artery originally as a coronary artery is reduced.

Note that, in the embodiment described heretofore, although a total of five paths including three paths A1 to A3 associated with the resolution and paths C1 and C2 associated with the CT value are used, the number of paths may be changed appropriately.

The technical concept of extracting a blood vessel by using the convolutional neural network 600 is not necessarily restricted to the coronary artery, and is also applicable to extraction of a blood vessel of other parts. Moreover, in a case in which it is possible to extract a blood vessel with a relatively high accuracy by using only the paths A1 to A3 (may be only two paths) of resolution and not using the paths C1 and C2 of the CT value, the paths C1 and C2 may be omitted.

Moreover, heretofore, although the description was made by referring mainly to extraction of a blood vessel, it is also possible to apply the technical concept of the present invention to other anatomical structures such as body organs and bones.

[Learning Phase]

Figure 9:
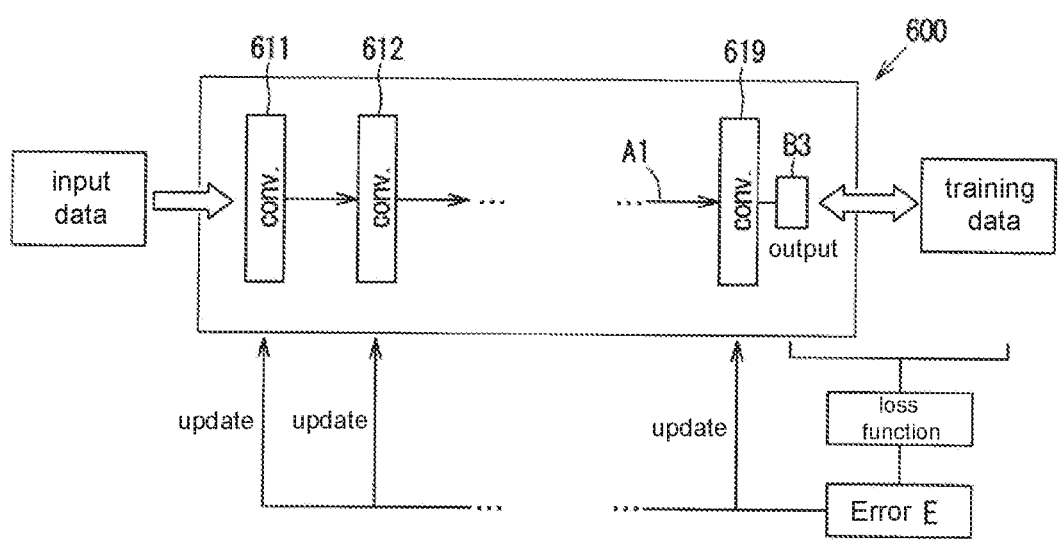
FIG. 9 is a diagram for explaining learning of the convolutional neural network in FIG. 3.

Next, learning of the weight parameters of the convolutional neural network 600 as mentioned above will be described. The description will be made by reducing to an example of the path A1 by referring to FIG. 9.

A three-dimensional filter is set to each of the convolutional layers 611 to 619, and the three-dimensional filter includes the weight parameters. Specifically, if it is a three-dimensional filter of 3×3×3, it includes $3^3=27$ filter parameters. Moreover, regarding the fully connected layers, parameters indicating connecting strength of the nodes (not shown) are included.

For learning, a set of training data is to be prepared. In the present embodiment, as the training data, it is possible to use coronary artery volume data achieved by extracting a blood vessel manually by a doctor while looking at actual data, on the basis of a certain medical volume data 601. A plurality of such pairs of the medical volume data 601 and coronary artery volume data extracted therefrom are to be prepared and let to be the set of training data.

Moreover, using an output value when a certain medical volume data 601 is input for the convolutional neural network 600 and a value of the training data, and using a predetermined error function (loss function), the learning is to be repeated till that error E becomes adequately small.

The error function is not restricted in particular, and it is possible to use a mean square error etc. A method for making the error E small is not restricted in particular, and it may be a method in which parameters are sequentially updated by using a gradient descent method. As a function for evaluating the degree of similarity of the sets of data, Jaccard index, Sorensen-Dice coefficient, Overlap coefficient (Szymkiewicz-Simpson coefficient), and the like may be used. In the learning of the gradient descent method, naturally, without using all data for learning at one time, a so-called mini batch learning in which only some samples are used in sequence may be used.

By the above series of learning processes, it is possible to optimize the parameters of the convolutional neural network 600 to an adequate accuracy. From a view point of an efficiency of learning, in a case in which the two paths C1 and C2 for which the range of CT values is let to differ are provided as in the present embodiment, an ability to carry out learning with even lesser number of training data can be anticipated.

Heretofore, an aspect of the present invention has been described by citing specific examples; however, the present invention can be modified appropriately without departing from the scope of the present invention:

Data Augmentation

Regarding the data to be used for learning, it is preferable to increase the number of data by data augmentation, and to carry out the learning. As a method of data augmentation, apart from methods such as shift, rotation, and zoom, for instance, a non-rigid deformation in which, shape data and vector data are deformed, may be used. Even if it is a relatively small amount of data, by using the data augmentation effectively, it is possible to carry out effective learning and to facilitate improvement in the accuracy of blood vessel extraction.

Input of Different Data for Learning for Different Paths

In the abovementioned embodiment, the neural network structure including three paths A1 to A3 with different resolution were described. Here, for instance, a case of making learn ten volume data in order will be taken into consideration. In this case, common volume data '1' may be input to each of the paths A1 to A3 upon changing the resolution; however, the following method is conceivable to be more effective. In other words, in a case of the method of inputting the volume data '1' to each of the paths A1 to A3, since the reduced images can be almost similar, there is a concern that learning efficiency in each path becomes relatively low. In that case, an arrangement may be made to input different data for learning to each path (or each of a certain path group and the other path group). More specifically, at the time of the mini batch learning for instance, by making the abovementioned arrangement of inputting different batch data to each of the paths A1 to A3, improvement of learning in each path can be anticipated.

In the embodiment described above, the description was made for the three-dimensional voxel data; however, if necessary, the technology of the present invention may be applied to three-dimensional data. The main constituent which carries out the learning and/or which carries out the blood vessel extraction is not necessarily required to be a single computer, and may be a plurality of computers.

Note that, in the present application, although the description was carried out basically by the name 'blood vessel extraction apparatus', the subject of the present invention is not necessarily restricted to such name, and may be expressed as 'image processing apparatus', or, the term 'apparatus' may be replaced by a term such as 'device' and 'system'.

(Note)
(Appended Mode)

The present application discloses the following invention. Note that, reference numerals in brackets are assigned for reference, and the present invention is not restricted thereby.

1. An apparatus (400) comprising:
an image processing unit (450) which extracts from medical volume data (601), a blood vessel included in the medical volume data (601), wherein
the convolutional neural network (600) includes
a convolutional unit (600*a*) having
a1: a first path (A1) including a plurality of convolutional layers (conv), to which, data (51) for a first target region (R1) including some target voxels (681*a*) in the medical volume data, is input at a first resolution, and
a2: a second path (A2) including a plurality of convolutional layers (conv), to which, data (52) for a second target region (R2) including some target voxels (681*a*) in the medical volume data, is input at a second resolution, and
b: an output unit (600*b*) having a neural net structure, which outputs numerical values related to visualization of the target voxels (681*a*) with an output result of the first path and the second path as input data.

According to an aspect of the present invention, in such manner, since the volume data of different resolution is input to the paths (A1, A2 etc.) parallel in the convolutional neural network, and a numerical value related to the visualization of the target voxel is to be achieved (it is not restricted, and display or non-display of the voxel and a display density may be determined on the basis of that numerical value), it is possible to carry out the extraction of the object with high accuracy.

2. Furthermore, the convolutional neural network further includes as the convolutional unit (600*a*).
c1: a first additional path (C1) including a plurality of convolutional layers, to which, data (54) for a target region including some target voxels (681*a*) in the medical volume data, in which CT values of the medical volume data (601) have been clipped within a first range, is input, and
c1: a second additional path (C2) including a plurality of convolutional layers, to which, data (55) for a target region including some target voxels (681*a*) in the medical volume data, in which CT values of the medical volume data (601) have been clipped within a second range, is input.

3. The first range is a range of which an upper limit is let to be 500 HU, and the second range is a range of which a lower limit is let to be 300 HU.

In such manner, letting one of the ranges to be a range of relatively low CT values, and the other to be a range of relatively high CT values, and by carrying out the convolution processing separately for these ranges, an ability to execute the machine learning separately can be anticipated.

4. The convolutional neural network further includes as the convolutional unit (600*a*),
a3: a third path (A3) including a plurality of convolutional layers, to which, data (53) for a third target region (R3) including some target voxels (681*a*) in the medical volume data, is input at a third resolution.

5. The image processing unit (450) is configured to determine a display mode of the voxel on the basis of the numerical value (example: 080) related to the visualization, and to display a blood vessel on the basis thereof.

6. The blood vessel is a coronary artery, and the medical volume data is data of a range including at least a heart and a coronary artery.

7. A blood vessel extraction method which is a method of extracting from medical volume data (601), a blood vessel in the medical volume data by using a convolutional neural network (600), wherein
the convolutional neural network (600) includes
a convolutional unit (600*a*) having
a1: a first path (A1) including a plurality of convolutional layers (conv), to which, data (51) for a first target region (R1) including some target voxels (681*a*) in the medical volume data, is input at a first resolution, and
a2: a second path (A2) including a plurality of convolutional layers (conv), to which, data (52) for a second target region (R2) including some target voxels (681*a*) in the medical volume data, is input at a second resolution, and
b: an output unit (600*b*) having a neural net structure, which outputs numerical values related to visualization of the target voxels (681*a*) with an output result of the first path and the second path as input data.

8. A blood vessel extraction program which is a computer program for extracting from medical volume data, a blood vessel in the medical volume data (601) by using a convolutional neural network (600), wherein
the convolutional neural network (600) includes
a convolutional unit (600*a*) having
a1: a first path (A1) including a plurality of convolutional layers (conv), to which, data (51) for a first target region (R1) including some target voxels (681*a*) in the medical volume data, is input at a first resolution, and
a2: a second path (A2) including a plurality of convolutional layers (cony), to which, data (52) for a second target region (R2) including some target voxels (681*a*) in the medical volume data, is input at a second resolution, and
b: an output unit (600*b*) having a neural net structure, which outputs numerical values related to visualization of the target voxels (681*a*) with an output result of the first path and the second path as input data.

The invention according to an aspect of the present invention may be as follows:

A1. An apparatus (400) comprising:
an image processing unit (450) which extracts from medical volume data (601), an anatomic structure in the medical volume data (601), wherein
the convolutional neural network (600) includes
a convolution unit (600*a*) having
a1: a first path (A1) including a plurality of convolutional layers (conv), to which, data (51) for a first target region (R1) including some pixels of interest (681a) in the medical volume data, is input at a first resolution, and a2: a second path (A2) including a plurality of convolutional layers (conv), to which, data (52) for a second target region (R2) including some pixels of interest (681a) in the medical volume data, is input at a second resolution.

The anatomic structure is not restricted to a blood vessel and may be a body organ, a bone etc.

A2. (The convolutional neural network (600)) further includes b: an output unit (600b) having a neural net structure, which outputs numerical values related to visualization of the target pixel (681a) with an output result of the first path and the second path as input data.

Note that in the present specification, one technical component can be combined appropriately with another technical component without departing from the scope of the present invention. Moreover, the content described as the invention of an apparatus for example, can also be expressed as an invention of a method and an invention of a computer program (computer program medium).

DESCRIPTION OF REFERENCE NUMERALS 11 heart
12 coronary artery
13 another blood vessel
100 chemical-liquid injector
110 injection head
150 console
400 blood vessel extraction apparatus
450 image processing unit
600 convolutional neural network
600a convolution unit
600b output unit
601 medical volume data
611-619 convolutional layer
A1-A3 path
B1-B2 fully connected layer
B3 output layer
C1-C2 additional path

The invention claimed is:

1. A blood vessel extraction apparatus comprising:
an image processing unit which extracts a blood vessel from medical volume data using a convolutional neural network, wherein the convolutional neural network includes
a convolutional unit having:
a1: a first path including a plurality of convolutional layers to which data for a first target region including some target voxels in the medical volume data is input at a first resolution;
a2: a second path including a plurality of convolutional layers to which data for a second target region including some target voxels in the medical volume data is input at a second resolution; and
b: an output unit having a neural net structure which outputs numerical values related to visualization of the target voxels with an output result of the first path and the second path as input data,
wherein the convolutional neural network further includes one of
c1: a first additional path including a plurality of convolutional layers to which data for a target region including some target voxels in the medical volume data in which CT values of the medical volume data have been clipped within a first range is input, or
c2: a second additional path including a plurality of convolutional layers to which data for a target region including some target voxels in the medical volume data in which CT values of the medical volume data have been clipped within a second range is input.

2. The blood vessel extraction apparatus according to claim 1, wherein the convolutional neural network includes both of the:
first additional path and the second additional path.

3. The blood vessel extraction apparatus according to claim 1,
wherein the first range is a range in which an upper limit is 500 HU, and
the second range is a range in which a lower limit is 300 HU.

4. The blood vessel extraction apparatus according to claim 2,
wherein the convolutional neural network further includes as the convolutional unit:
a3: a third path including a plurality of convolutional layers to which data for a third target region including some target voxels in the medical volume data, is input at a third resolution.

5. The blood vessel extraction apparatus according to claim 1, wherein the image processing unit is configured to determine a display mode of the voxels on the basis of numerical values related to the visualization, and to display a blood vessel on the basis thereof.

6. The blood vessel extraction apparatus according to claim 1, wherein the blood vessel is a coronary artery and the medical volume data is a data of a range including at least a heart and a coronary artery.

7. A blood vessel extraction method which is a method of extracting a blood vessel in medical volume data using a convolutional neural network, wherein
the convolutional neural network includes
a convolutional unit having
a1: a first path including a plurality of convolutional layers, to which, data for a first target region including some target voxels in the medical volume data is input at a first resolution;
a2: a second path including a plurality of convolutional layers to which data for a second target region including some target voxels in the medical volume data is input at a second resolution; and
b: an output unit having a neural net structure, which outputs numerical values related to visualization of the target voxels with an output result of the first path and the second path as input data
wherein the convolutional neural network further includes one of
c1: a first additional path including a plurality of convolutional layers to which data for a target region including some target voxels in the medical volume data in which CT values of the medical volume data have been clipped within a first range is input, or
c2: a second additional path including a plurality of convolutional layers to which data for a target region including some target voxels in the medical volume data in which CT values of the medical volume data have been clipped within a second range is input.

8. A non-transitory computer-readable medium storing blood vessel extraction program which is a computer program for extracting a blood vessel included in medical volume data using a convolutional neural network, wherein the convolutional neural network includes
a convolutional unit having
- a1: a first path including a plurality of convolutional layers to which data for a first target region including some target voxels in the medical volume data is input at a first resolution;
- a2: a second path including a plurality of convolutional layers to which data for a second target region including some target voxels in the medical volume data is input at a second resolution; and
- b: an output unit having a neural net structure, which outputs numerical values related to visualization of the target voxels with an output result of the first path and the second path as input data wherein the convolutional neural network further includes one of
- c1: a first additional path including a plurality of convolutional layers to which data for a target region including some target voxels in the medical volume data in which CT values of the medical volume data have been clipped within a first range is input, or
- c2: a second additional path including a plurality of convolutional layers to which data for a target region including some target voxels in the medical volume data in which CT values of the medical volume data have been clipped within a second range is input.

* * * * *

UNITED STATES PATENT AND TRADEMARK OFFICE
CERTIFICATE OF CORRECTION

PATENT NO. : 11,392,793 B2
APPLICATION NO. : 16/651885
DATED : July 19, 2022
INVENTOR(S) : Kazumasa Masuda et al.

It is certified that error appears in the above-identified patent and that said Letters Patent is hereby corrected as shown below:

On the Title Page

Page 2, Column 2 (Other Publications), Line 9, delete "for for" and insert -- for --.

In the Specification

Column 5, Line 15, delete "461," and insert -- 461. --.

Column 6, Line 32, delete "3x3x" and insert -- 3x3x3 --.

Column 7, Line 30, delete "center," and insert -- center. --.

Column 8, Line 34, delete "layer B1," and insert -- layer B1. --.

Column 8, Line 47, delete "artery;" and insert -- artery, --.

Column 11, Line 57, delete "(600a)." and insert -- (600a), --.

Column 12, Line 51, delete "(cony)," and insert -- (conv), --.

Signed and Sealed this
Twenty-eighth Day of February, 2023

Katherine Kelly Vidal
*Director of the United States Patent and Trademark Office*